US006989674B2

(12) United States Patent
Wind et al.

(10) Patent No.: US 6,989,674 B2
(45) Date of Patent: Jan. 24, 2006

(54) ADVANCED SLOW-MAGIC ANGLE SPINNING PROBE FOR MAGNETIC RESONANCE IMAGING AND SPECTROSCOPY

(75) Inventors: Robert A. Wind, West Richland, WA (US); Jian Zhi Hu, Richland, WA (US); Kevin R. Minard, Kennewick, WA (US); Donald N. Rommereim, Pasco, WA (US)

(73) Assignee: Battelle Memorial Institute, Richland, WA (US)

( * ) Notice: Subject to any disclaimer, the term of this patent is extended or adjusted under 35 U.S.C. 154(b) by 0 days.

(21) Appl. No.: 10/639,828

(22) Filed: Aug. 12, 2003

(65) Prior Publication Data

US 2005/0035766 A1 Feb. 17, 2005

(51) Int. Cl.
*G01V 3/00* (2006.01)
(52) U.S. Cl. ..................... 324/321; 324/318
(58) Field of Classification Search ............... 324/321, 324/318, 322, 309, 307
See application file for complete search history.

(56) References Cited

U.S. PATENT DOCUMENTS

| | | | | |
|---|---|---|---|---|
| 5,208,536 | A | * | 5/1993 | Cory .......................... 324/321 |
| 5,298,864 | A | * | 3/1994 | Muller et al. ............... 324/321 |
| 5,754,048 | A | | 5/1998 | Bielecki |
| 5,872,452 | A | * | 2/1999 | Cory et al. .................. 324/321 |
| 2002/0125887 | A1 | | 9/2002 | Wind et al. |
| 2003/0052678 | A1 | | 3/2003 | Gerald, II et al. |
| 2003/0102867 | A1 | | 6/2003 | Hioka |

FOREIGN PATENT DOCUMENTS

EP  0 562 865 A1  9/1993

OTHER PUBLICATIONS

Ericsson A, Weis J, Hemmingsson A, Wikstrom M, and Sperber GO, Measurements of magnetic-field variations in the human brain using a 3D-FT multiple gradient-echo technique. Magn. Reson Med. 1995; 33: 171-177.

Yablonskiy DA, Quantitation of intrinsic magnetic susceptibility-related effects in a tissue matrix. Phantom study. Magn. Reson. Med. 1998; 39: 417-428.

(Continued)

*Primary Examiner*—Brij B. Shrivastav
(74) *Attorney, Agent, or Firm*—James D. Matheson

(57) ABSTRACT

The present invention relates to a probe and processes useful for magnetic resonance imaging and spectroscopy instruments. More particularly, the invention relates to a MR probe and processes for obtaining resolution enhancements of fluid objects, including live specimens, using an ultra-slow (magic angle) spinning (MAS) of the specimen combined with a modified phase-corrected magic angle turning (PHORMAT) pulse sequence. Proton NMR spectra were measured of the torso and the top part of the belly of a female BALBc mouse in a 2T field, while spinning the animal at a speed of 1.5 Hz. Results show that even in this relatively low field with PHORMAT, an isotropic spectrum is obtained with line widths that are a factor 4.6 smaller than those obtained in a stationary mouse. Resolution of $^1$H NMR metabolite spectra are thus significantly enhanced. Results indicate that PHORMAT has the potential to significantly increase the utility of $^1$H NMR spectroscopy for in vivo biochemical, biomedical and/or medical applications involving large-sized biological objects such as mice, rats and even humans within a hospital setting. For small-sized objects, including biological objects, such as excised tissues, organs, live bacterial cells, and biofilms, use of PASS at a spinning rate of 30 Hz and above is preferred.

5 Claims, 10 Drawing Sheets

OTHER PUBLICATIONS

Boxerman JL, Weisskopf RM, and Rosen BR, Susceptibility effects in whole body experiments. In: Young IR, editor. Methods in biomedical magnetic resonance imaging and spectrscopy. New York: John Wiley & Sons; 2000. p 654-661.

Kreis R., Quantitative localized $^1$H MR spectroscopy for clinical use, J. Progr. in NMR Spectr. 1997; 31: 155-195.

Garrod S, Humpfer E, Spraul M, Connor SC, Polley S, Connelly J, Lindon JC, Nicholson JK and Holmes E. High-resolution magic angle spinning $^1$H NMR spectroscopic studies on intact rat renal cortex and medulla. Magn Reson Med 1999; 41: 1108-1118.

Bollard ME, Garrod S, Holmes E, Lindon JC, Humfer E, Spraul M and Nicholson JK. High-resolution $^1$H and $^1$H-$^{13}$C magic angle spinning NMR spectroscopic of rat liver. Magn Reson Med 2000; 44: 201-207.

Andrew ER, Eades RG. Removal of dipolar broadening of NMR spectra of solids by specimen rotation. Nature 1959; 183: 1802.

Garroway AN. Magic-angle sample spinning of liquids. J. Magn Reson 1982; 49: 168-171.

VanderHart DL. Magnetic susceptibility & high resolution NMR of liquids & solids. In: Grant DM Harris RK, editors. Encyclopedia of nuclear magnetic resonance. New York: John Wiley & Sons; 1996. p 2938-2946.

Weybright P, Millis K Campbell N, Cory DG, and Singer S, Gradient, high-resolution, magic angle spinning $^1$H nuclear magnetic resonance spectroscopy of intact cells, Magn. Reson. Med. 1998; 39: 337-345.

Chen J, Enloe BM, Fletcher CD, Cory DG, Singer S. Biochemical Analysis Using High-Resolution Magic Angle Spinning NMR Spectroscopy Distinguishes Lipoma-like Well-differentiated Liposarcoma from Normal Fat. J Am Chem Soc 2001; 123: 9200-9201.

Garrod S, Humpher E, Connor SC, Connelly JC, Spraul M, Nicholson JK, and Holmes E. High-resolution $^1$H NMR and magic angle spinning NMR spectroscopy investigation of the biochemical effects of 2-bromoethanamine in intact renal and hepatic tissue. Magn Reson Med 2001; 45: 781-790.

Wind RA, Hu JZ, and Rommereim DN, High Resolution $^1$H NMR Spectroscopy in Organs and Tissues Using Slow Magic Angle Spinning, Magn. Reson. Med. 2001; 46: 213-218.

Hu JZ, Rommereim DN, and Wind RA, High Resolution $^1$H NMR Spectroscopy in Rat Liver Using Magic Angle Turning at a 1 Hz Spinning Rate, Magn. Reson. Med. 2002; 47: 829-836.

Hu JZ and Wind RA, The evaluation of different MAS techniques at low spinning rates in aqueous samples and in the presence of magnetic susceptibility gradients, J. Magn. Reson. 2002; 159: 92-100.

Oyama AJ, Response and adaptation of Beagle dogs to hypergravity, Life sciences and space research XIII: Proc. of the 17$^{th}$ plenary meeting, Sao Paulo, Brazil 1974, Akademie-Verlag, Berlin, 1975. p. 11-17.

\* cited by examiner

ADVANCED SLOW-MAGIC ANGLE SPINNING PROBE FOR MAGNETIC RESONANCE IMAGING AND SPECTROSCOPY

The invention was made with Government support under Contract DE-AC0676RLO 1830, awarded by the U.S. Department of Energy. The Government has certain rights in the invention.

BACKGROUND OF THE INVENTION (1) Field of the Invention

The present invention relates to a device for magnetic resonance (MR) imaging and spectroscopy of fluid-based objects, generally. More particularly, the present invention relates to a new slow "magic angle" spinning (slow-MAS) probe useful for Magnetic Resonance (MR) imaging and spectroscopy of biological objects, including live animals.

(2). Description of the Technical Art

In vitro and in vivo $^1$H NMR spectroscopy are widely used for investigating biochemical processes in cells, tissues, animals, and humans (see, for example, I. R. Young, ed., methods in Biomedical magnetic resonance imaging and spectroscopy). However, the $^1$H spectrum obtained from a static sample often suffers from poor resolution due to various line broadening mechanisms inherent within a biological system. This hampers a quantitative, and sometimes even qualitative, analysis of the spectra. And, it is found that when intact objects such as cells, cell systems, tissues, organs, and living specimens (e.g., "biological objects") are placed in an external magnetic field, variations in the isotropic bulk magnetic susceptibility near the boundaries of inter- and intra-cellular structures induce local magnetic field gradients in the objects. While these susceptibility gradients can sometimes provide useful medical information, they also broaden the NMR lines. This is especially true for $^1$H NMR spectroscopy where resulting spectra often contain severely overlapping spectral lines that can seriously hamper both the qualitative and quantitative spectral analysis. Increasing the $T_2$ weighting factors can sometimes enhance the spectral resolution, but can also result in serious signal losses and spectral distortions.

It is well known in the art that susceptibility broadening can be averaged to zero by the technique known as Magic-Angle Spinning (MAS), whereby a sample or specimen is rotated about an axis positioned at an angle of 54°44' relative to the external magnetic field $B_0$. In a standard MAS experiment, a single 90° radio frequency (RF) pulse is used to observe the signal. The spinning frequency is typically chosen equal to or greater than the spectral width to avoid spectral spinning sidebands (SSBs) that can surround the various resonance peaks. Of particular concern are SSBs associated with the residual water signal. For example, if a lower spinning frequency is used, water SSBs can overlap with the metabolite lines rendering the interpretation of the spectra difficult. Spinning rates varying from several kHz to more than 10 kHz have been used to obtain high-resolution $^1$H MAS metabolite spectra in cells and excised tissues. However, techniques are required that separate or eliminate the SSBs from these high-resolution metabolite spectra.

A serious problem associated with conventional fast-MAS spectroscopy of fluid-filled objects (including live specimens) is the introduction of large centrifugal forces ($F_c$) that can be induced in a sample from the high spinning rates. For example, spinning can destroy the tissue structure and even individual cells. The centrifugal force $F_c$ is given by $F_c=m\omega^2 r$, where m is the mass, $\omega=2\pi F$, F is the spinning frequency, and r is the distance from the rotational axis to the point of interest. As an example, when F=2 kHz and r=1 cm, $F_c$ can equal $1.6\times10^5$ times the gravitational force G. Thus, standard MAS spectroscopic methods are not viable for the study of intact and/or larger biological objects, samples, or specimens and more particularly in vivo studies. Rotating a specimen under slow-, or ultra-slow, spinning speeds will not affect the fluid object. Gravitational forces are low in such experiments, even in larger objects such as animals. For example, a small mouse spun at a frequency of 1 Hz experiences a maximum gravitational force effect at its perimeter of only 0.04 G (at a maximal distance of about 1 cm from the rotational axis). And, centrifuge experiments conducted on dogs and rats [see, for example, Oyama et al., *Response and Adaptation of Beagle Dogs to Hypergravity, Life sciences and Space Research XIII: Proc. of the 17th Plenary Meeting*, Sao Paulo, Brazil 1974, Akademie-Verlag, Berlin, 1975. p. 11–17 and Wunder et al., *Knee-Ligament Loading Properties as Influenced by Gravity: I-Junction with Bone of 3-G Rodents*: Aviation, Space, and Environm. Med. 1982; 53: 1098–1111) at the maximum allowable centrifugal force (a value of 2.5–3 G) suggest that a mouse may be spun at speeds of up to 8.6 Hz.

Commercially available magic angle spinning (MAS) probes are largely aimed at achieving sample spinning rates on the order of several hundred Hz or greater because the primary application of the MAS probes is almost entirely applied in the field of solid state NMR. Thus, the current state-of-the-art teaches, and is directed to, increasingly higher spinning rates and increasingly higher magnetic field strengths in order to eliminate the spinning sidebands associated with various internal spin interactions. And, instruments with sample spin rates as high as 26 kHz, for example, are commercially available (Doty Scientific Inc.).

The probe of the present invention contrasts with the current state-of-the-art in that the selection of spin rates is at substantially lower spin frequencies so as to be operable for MR Imaging and Spectroscopy on fluid-objects, and more preferably on biological objects.

In a recent attempt to test the applicability and viability of commercial systems, we made modifications to an existing Varian-Chemagnetics probe; spinning speeds as slow as 1 Hz were achieved. However, a slow, stable spin rate was not achieved in the modified commercial NMR probe over a sufficiently long time interval to be viable. Further still, the commercial probe routinely overshot the upper frequency boundary limit of 100 Hz for safe spinning upon initial startup, which proved unacceptable for research involving live objects, including live animals.

Recently we have been able to separate SSB's from the metabolites spectrum of interest in fluid objects by combining slow-MAS with special radio frequency (R.F.) pulse sequences using two methods originally developed for solid state NMR (Antzutkin et al. in J. Magn. Reson. 1995, A115: 7–19; and Hu J Z, Wang W, Liu F, Solum M S, Alderman D W, Pugmire R J, Grant D M. Magic-angle-turning experiments for measuring chemical-shift-tensor principal values in powdered solids. J. Magn. Reson. 1995, A113: 210–222). These include: 1) Phase Adjusted Spinning Sidebands (PASS) and 2) Phase-corrected Magic Angle Turning (PHORMAT). For example, we have modified and successfully applied two-dimensional sideband separation in magic-angle-spinning NMR on biological samples (R. A. Wind, J. Z. Hu, and D. N. Rommereim, "High Resolution $^1$H NMR Spectroscopy in Organs and Tissues Using Slow Magic Angle Spinning", Magn. Reson. Med. 46, 213–218 (2001), J. Z. Hu, D. N. Rommereim, and R. A. Wind, "High Resolution $^1$H NMR Spectroscopy in Rat Liver Using Magic Angle Turning at a 1 Hz Spinning Rate," Magn. Reson. Med. 47, 829–836 (2002)) hereby incorporated by reference.

It was found with PASS that spinning speeds as low as 40 Hz could be used, which makes the techniques amenable for small fluid objects such as cell agglomerates, excised tissues and organs. Similarly, with PHORMAT, the spinning speed could be reduced to 1 Hz, albeit with less sensitivity and a longer measuring time than with PASS. Still, PHORMAT is the only technique available to date for studying larger objects with slow MAS, including live animals. PHORMAT was recently demonstrated in a live mouse (R. A. Wind, J. Z. Hu, and D. N. Rommereim, "High resolution $^1$H NMR spectroscopy in a live mouse subjected to 1.5 Hz magic angle spinning," Magn. Reson. Med. (2003)). Previous patent applications regarding the slow-MAS methodology have been submitted (see US2002-0135365A1 and US2002-0125887A1), hereby incorporated in their entirety herein by this reference. Although these applications comprehensively describe the general procedures of the slow-MAS methodology, nowhere do they describe a slow-MAS probe suitable for applying the methodology to a fluid biological object.

Accordingly, there remains a need for a "magic-angle" spinning probe useful for high resolution magnetic resonance imaging and spectroscopy of fluid objects. More specifically, there remains a need for a slow Magic Angle Spinning probe that allows for the mounting of biological objects, including live intact specimens, having well-controlled, stable spinning rates whereby high resolution MR imaging and spectroscopy may be conducted under conditions that do not damage the tissues or cellular structure of the objects and that still further minimizes and avoid problems associated with SSBs at the required slow spinning rates, and that allows for increasing sizes of an object.

SUMMARY OF THE INVENTION

The present invention relates to a device for magnetic resonance imaging (MRI), localized magnetic resonance spectroscopy (MRS), and spectroscopic or chemical shift imaging (CSI) of fluid-based objects, generally. More particularly, the present invention relates to a slow Magic Angle Spinning (slow-MAS) probe useful for in vivo MR imaging and spectroscopy of biological objects (including live animals). Fluid-filled objects of interest include biological objects (cells, cell aggregates, cell systems, tissues, organs, and the like) as well as live specimens of a size and shape that include a potential human patient.

Specimens and/or fluid based objects may be mounted for the first time in a novel slow-Magic Angle Spinning (slow-MAS) probe ("the probe") containing the gradient coils, the necessary radio frequency (R.F) circuitry, and a rotor (spinning) system capable of rotating the specimen at the magic angle. The probe can be inserted in an external magnetic field, and rotated about an axis positioned at an angle of 54°44' (or 54.74°, the so-called magic angle) relative to the external magnetic field ($B_o$). Spinning speeds of less than a bout 100 Hz, more preferably up to about 40 Hz, and most preferably in the range from 0.01 Hz to 40 Hz may be employed, being sufficiently low to prevent damage to the structural integrity of an object or animal that can result from centrifugal forces associated with spinning. The slow-MAS probe provides for enhanced spectral resolution on a rotating object useful for MRI, MRS, and CSI using special techniques such as 2-D PASS and PHORMAT to obtain SSB-free high resolution and water suppressed metabolite spectra of specific volumes in the object. Further, the probe is of a modular design, and its dimensions and the dimensions of the various probe components can be adapted for use on small (sub-mm), medium-to-large (tens of cm), and potentially large (>60 cm) fluid and biological objects.

While the present invention is described herein with reference to the preferred embodiments thereof, it should be understood that the invention is not limited thereto, and various alternatives in form and detail may be made therein without departing from the spirit and scope of the invention. In particular, those skilled in the art will appreciate that the components of the shielding, gradient coil(s), rotor assembly used to mount fluid objects (e.g., live animal specimens for example), and/or other allied components (console, optical detection system, monitoring system, etc.) as described herein, can be of varying dimensions to accommodate the variability in size and shape of the specimens, and/or to probe the varied parameters of interest, or to collect data related to the same. Thus, no limitation in scope is intended by reference to the preferred embodiments herein.

BRIEF DESCRIPTION OF THE DRAWINGS

A more complete appreciation of the invention will be readily obtained by reference to the following description of the accompanying drawings in which like numerals in different figures represent the same structures or elements.

DETAILED DESCRIPTION OF THE INVENTION

The following terms and definitions are intended to aid the reader, but should not be construed to have a scope less than that understood by persons of ordinary skill in the art, or as limiting the scope of the appended claims:

"Object" refers typically to a three-dimensional object such as a spectroscopic sample (such as that taken from a tissue or cellular material), a bulk animal tissue, an animal organ, or a live intact animal or specimen.

"Fluid Object" means an object that includes a substantial amount of fluid, as opposed to a solid object. Such objects comprise fluids at or exceeding 50 wt % water. For example, cells, cellular matter, tissues, organs, organ systems, and live animals (including human patients).

"Biological Object" means any object, usually a fluid object, that includes cellular matter. Biological objects include cells, cell systems, tissues, intact organs, lives animals, and a body of a human patient.

Figure 1:
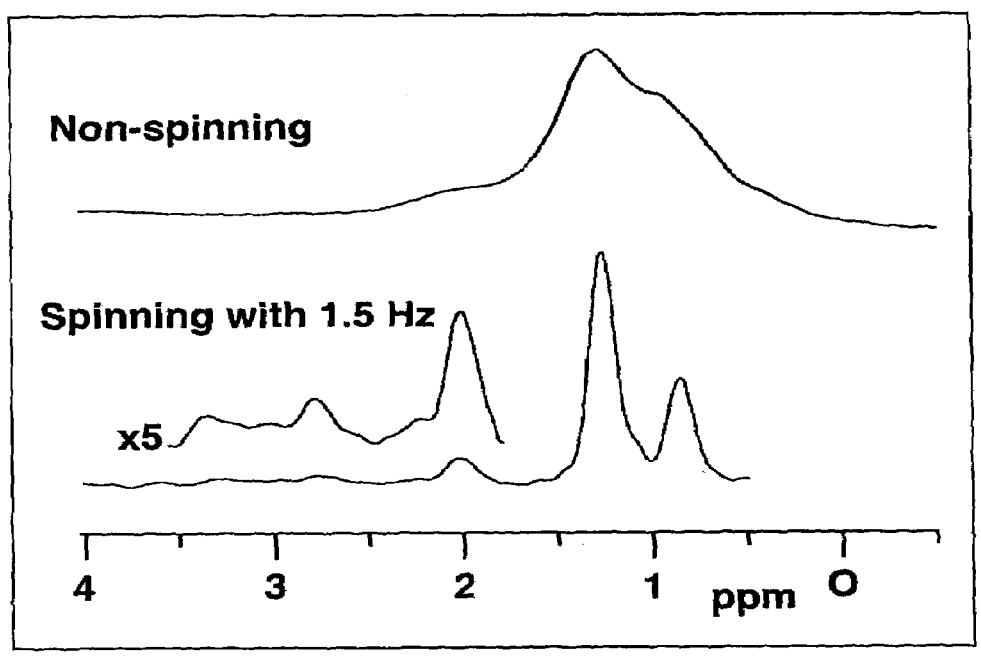
FIG. 1 illustrates the spectral resolution enhancement obtained with slow-Magic Angle Spinning Magnetic Resonance imaging and spectroscopy of a live mouse spinning at 1.5 Hz in a 2 Tesla external field compared with non-spinning.

FIG. 1 shows the spectral resolution enhancement proffered by a slow MAS probe spinning under slow magic angle spinning (MAS) conditions, as compared with non spinning conditions, evidencing the strong utility of the present invention.

Figures 2, 2A, 2B:
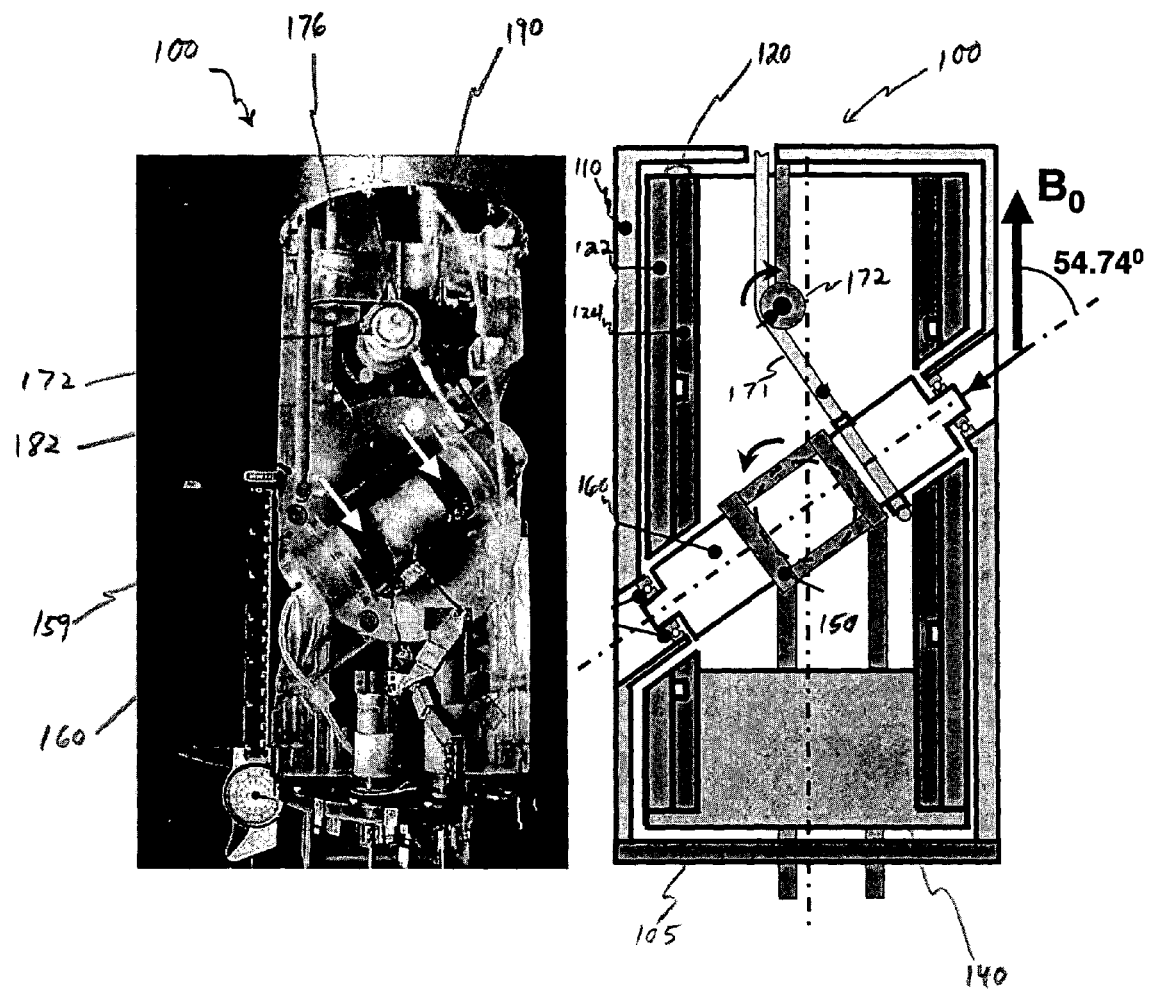
FIG. 2A illustrates a slow-MAS probe without a gradient coil assembly (e.g., incorporated gradient coils) according to one embodiment of the present invention, capable of studying a sectional portion of a fluid filled object, e.g., a mouse body, as indicated by the arrows.
FIG. 2B shows a diagrammatic illustration of the elements of a slow-MAS probe with an incorporated gradient coil assembly according to a second embodiment of the present invention, capable of studying a whole fluid filled object, e.g., a full mouse body.

FIGS. 2A and 2B illustrate a slow MAS probe 100 according to two different embodiments of the present invention, e.g., with (FIG. 2B) and without (FIG. 2A) a gradient coil(s) assembly 120, respectively.

In a preferred embodiment (FIG. 2B), the slow MAS probe 100 comprises at least one supporting (base) member 105; a shielding member 110 having a gradient coil(s) assembly 120 for containing a plurality of gradient coils. The gradient assembly 120 further comprises a first (gradient) housing member 122 for containing x-gradient coil(s) and the y-gradient coil(s) and a second housing member 124 for containing z-gradient coil(s). The probe 100 additionally comprises an R.F circuitry assembly 140 comprising at least one N MR coil(s) 150 for effecting the necessary pulse sequencing (e.g., transmitting) and for receiving a signal; a rotor assembly (FIG. 4) 160 adapted for spinning a specimen and disposed so as to be in optimum alignment with the gradient assembly 120 coil(s) and NMR coil(s) 150; a driving assembly (FIG. 5) 170 for spinning and/or rotating the rotor assembly 160; optionally a directional (axis) mechanism 182 to effect adjustment of the spinning axis of the rotor assembly 160 to a desired angle. In a one embodiment, the probe 100 also includes an optical detection system 190 (e.g., a sensor comprising a scintillation fiber, for example) to select, monitor, and stabilize the spinning frequency of the rotor assembly 160.

The rotor assembly 160 is adapted for rotating a cylinder about an axis at a desired angle, preferably at a critical angle of 54.74° (magic-angle) relative to the external magnetic field ($B_0$). In one embodiment of the present invention (FIG. 2A), adjustment of the rotor assembly 160 to set the magic angle may be effected by incorporation of a directional (axis) mechanism 182. As one example, the directional axis mechanism 182 may comprise a rod connected at a first end to a supporting member 159 (FIG. 5) that is operably connected to the rotor assembly 160 inside the probe 100, and at a second end, to a fine-adjustment control (for example, a Vernier device, a micrometer, or other comparable device) adjustable from outside the probe 100.

In a preferred embodiment, the probe 100 also comprises a large NMR transmitter coil(s) 150 adapted for use as a receiver coil 150 in combination with the RF circuitry 140. For example, an NMR coil(s) 150 of a bird cage coil design or of an Alderman-Grant coil design. Alternatively, if the volume of interest is at or near the periphery of a mounted specimen, a surface coil(s) may also be incorporated in the RF circuitry 140 to collect surface measurements. Other NMR coil(s) 150 include comparable transmitter/receiver coil(s), solenoid coil(s), inductance coil(s), and combinations thereof. In addition, shimming of spurious signals may be effected by incorporation of shim probe(s) or shim coil(s).

Figure 3:
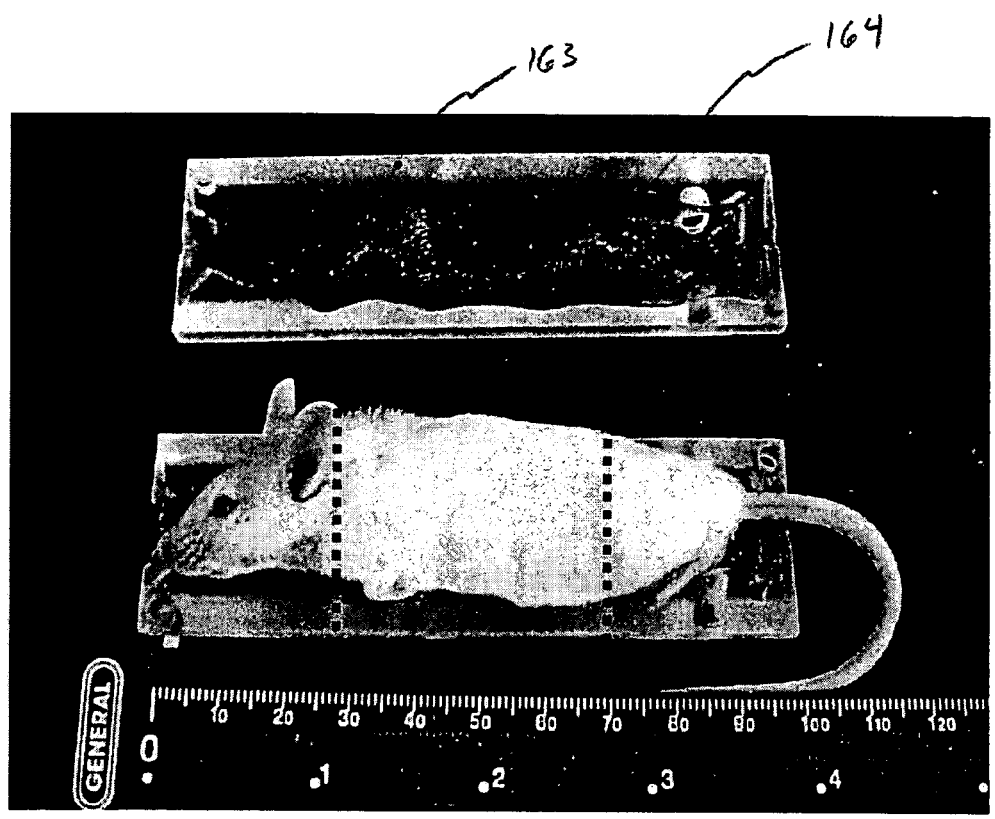
FIG. 3 illustrates a mouse mold according to one embodiment of the present invention.
Figures 4, 4A, 4B:
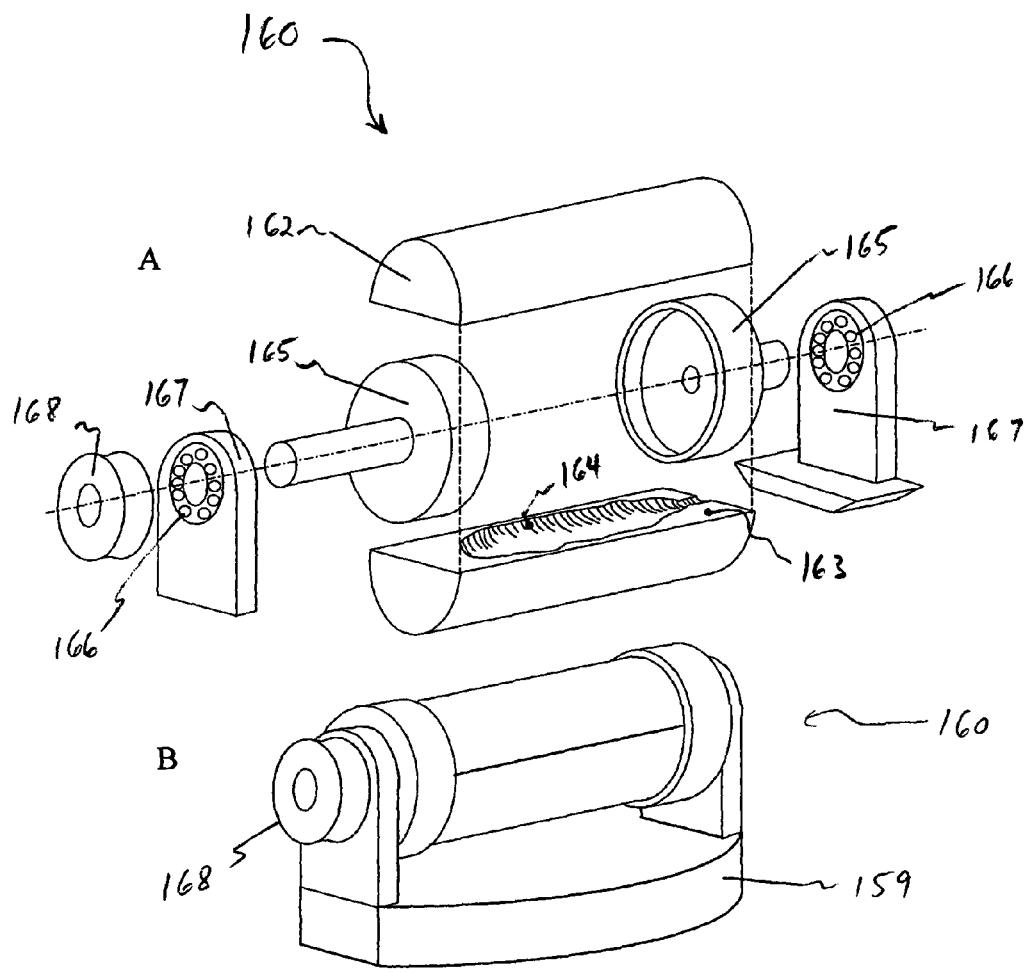
FIG. 4A illustrates an exploded view of a rotor assembly. This assembly will be adapted for use in a MAS-gradient NMR probe, according to an embodiment of the present invention.
FIG. 4B illustrates an assembled view of a rotor assembly. This assembly will be adapted for use in a MAS-gradient NMR probe, according to an embodiment of the present invention.

FIG. 4 illustrates an example of both an unassembled (FIG. 4A) and assembled view (4B) of the rotor assembly 160 of the slow-MAS probe 100 according to an embodiment of the present invention. As shown in FIG. 4B, the rotor 160 assembly comprises a cylinder 161 into which a specimen may be directly mounted. In a preferred embodiment, the cylinder 161 is adapted to receive a second cylinder 162 comprising an epoxy photopolymer cylindrical mold 163 into which a cavity 164 is introduced in a shape complementary to that of the specimen. The cavity 164 may be introduced stereo-lithographically into the mold 163, or by other similar or comparable techniques. The second cylinder 162 may be made from a variety of non-metallic materials, including, but not limited to plastics, resins, epoxy's, carbonates, polymers, and combinations thereof. In the case of an animal or other live specimen(s), the cavity 164 is preferably of a form whereby the animal fits snugly in the mold 163 to prevent motional artifacts in the NMR results and/or potential injury and damage to the animal from the rotation and/or centrifugal forces experienced during operation (e.g., spinning and/or rotation). FIG. 3 illustrates positioning of a live animal (e.g., mouse) so as to be mounted on a first half portion of the mold 163. The mold 163 can be shifted up and down in the cylinder 162 of the rotor assembly 160 such that the volume of interest (e.g., region to be probed) in the mouse is aligned at the center of the magnet providing the external magnetic field, the gradient coil(s) assembly 120, and the NMR coil 150. Further, the rotor assembly 160 may comprise a first and second rotor cap 165, ball bearings 166 housed in a first and second bearing mount 167 to stabilize the rotor 160; at least one pulley 168 adapted to receive and engage a drive belt 171 of the driving assembly (FIG. 5); a support member 159 for supporting the rotor assembly 160 so configured as to be rotatable about a vertical axis in order to adjust the desired angle, preferably to the magic angle. The bearings 166 are preferably of a non-metallic, non-magnetic material. For example, commercially available plastic bearings 166 (Jilson, Inc., Lodi, N.J.). Size of the bearings 166 is dependent on the desired speed of the rotor assembly 160 and also determines the maximum spinning speed that can be used for the probe 100. For frequencies up to 40 Hz, for example, the bearings 165 have a preferred I.D. dimension of 6.35 mm (~¼ in.). Larger and smaller bearings 165 may be incorporated and used depending on desired spin frequencies and/or size of the desired bore cylinder. Thus, no limitation in size is hereby intended by disclosure of the bearing size in the current example.

The rotor assembly 160 may further optionally comprise one or more openings (not shown). In a preferred embodiment, the opening(s) may be placed along a top portion of the assembly 160, serving as ventilation holes for a live specimen or animal mounted or secured in the mold 163 of the cylinder(s) [e.g., cylinder 161 or 162] during data collection, or to otherwise provide air circulation to the rotor assembly 160. In the present case, the probe 100 may also be configured with a compressor mounted into the probe to supply air or blow air into the rotor.

Figure 5:
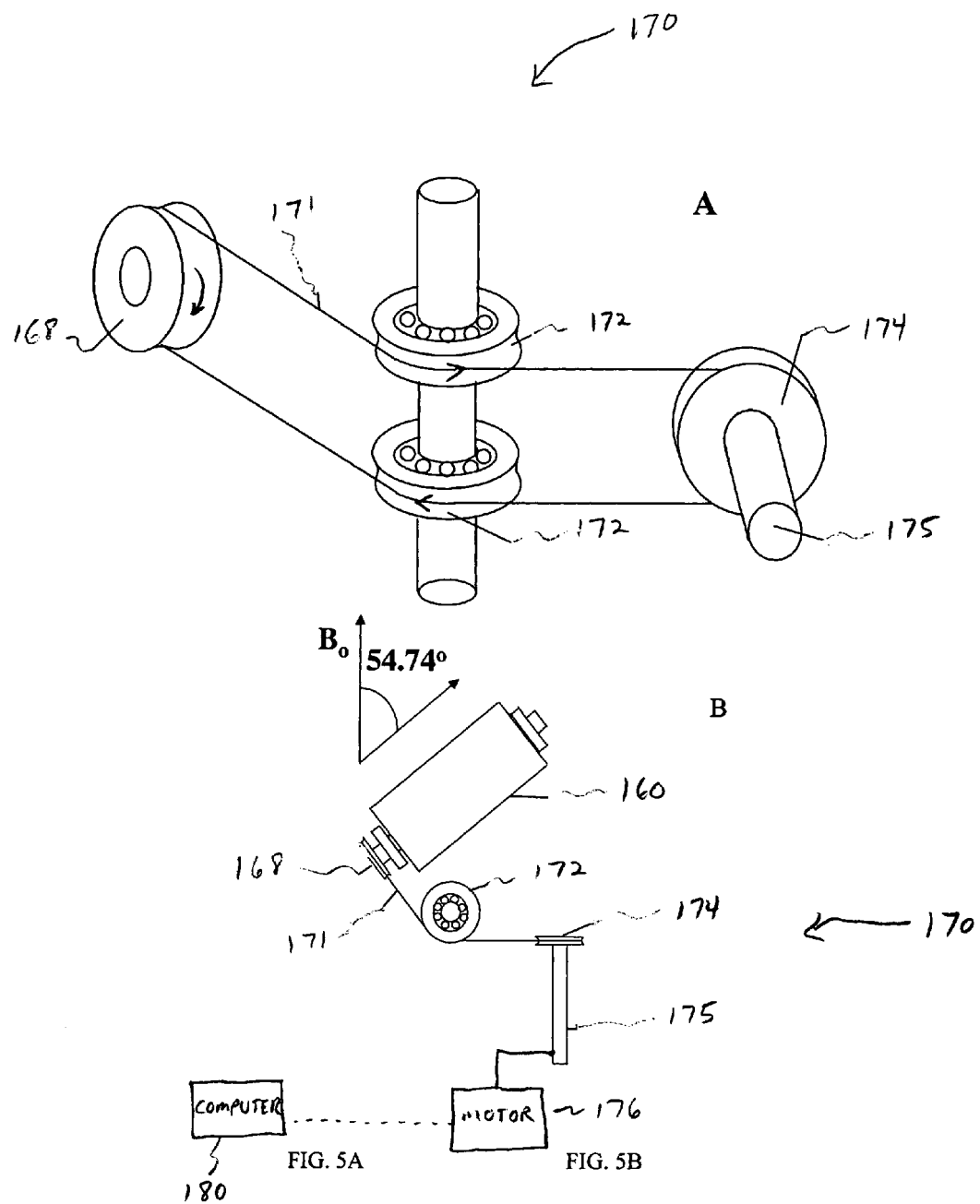
FIG. 5A illustrate a front view of a driving assembly consisting of pulleys and a drive belt. This assembly will be adapted for an MAS-NMR probe according to an embodiment of the present invention.
FIG. 5B illustrates a top view of a driving assembly consisting of a rotor, pulleys, and a drive belt. This assembly will be adapted for an MAS-NMR probe according to an embodiment of the present invention.

The probe 100 further comprises a driving (drive shaft) assembly 170 for driving the rotor assembly 160. FIG. 5 illustrates the rotor driving system 170 according to one embodiment of the present invention. FIGS. 5A and 5B present a front view and a top view, respectively, of the driving assembly 170.

The drive assembly 170 comprises a driving belt 171, first and second pulley members 172 comprising ball bearings 173; a third pulley member 174 disposed at the front (facing) the NMR magnet; and a driving shaft (rod) 175 fixed to the magnet pulley 174 at one end and preferentially connects operably with a driving motor 176. The first and second pulley members 172 are configured so as to rotate in opposite directions relative to one another, serving both to guide the drive belt 171 over an angle of approximately 125° and to adjust tension in the drive belt 171. The driving belt 171 further engages each of the various pulleys in the assembly 170.

In the preferred embodiment, as noted, the rotor assembly 160 is driven by a driving motor 176 disposed such that the rotor 160 axis is oriented about and along the magic axis. The driving assembly 170 makes it possible to precisely alter the rotation, speed, and/or direction of the rotor assembly 160 while collecting measurement data or performing in vivo experiments. In a preferred embodiment of the present invention, the driving motor 176 connected to the rotor assembly 160 is preferably controlled via a computer 180 for 1) effecting the pulse sequencing (e.g., RF, TTL, etc.) aspects of the invention, 2) controlling of other operational/control features/aspects of the probe and equipment, 3) performing data collection, analysis, and measurement functions/capabilities, and 4) setting the rotational frequency of the rotor assembly 160 up to a maximum of ~100 Hz. The driving motor 176 is further disposed distally preferably at a distance of about 2 meters from the MR magnet such that magnetic fringe fields generated by the magnet do not affect the performance of the motor 176.

Other components may be incorporated into the probe 100 as necessary, including a monitoring system for collecting sample measurement data. For example, a respiratory monitoring system may be configured to monitor, collect, and analyze respiratory motion data of an animal in respiratory-triggered NMR experiments. In another example, the probe 100 may be further configured for use with a respiratory monitoring system comprising a plethysmograph. For live specimens or animals, the probe 100 may also be configured with components to supply air to the rotor 160. For example, inclusion of a compressor and tubing to supply air to a live animal while the probe 100 is in operation. In a second example, the rotor assembly 160 may also be configured as a bioreactor in combination with necessary control elements such as temperature, nutrient supplies, pressure controls, etc. for in situ detection of biochemical processes inside a cell system.

The probe 100 is preferably interfaced, configured for use, and/or controlled via a computer 180 for automating, controlling the measurement and testing equipment, and collecting measurement data. For example, in a preferred embodiment, the driving motor 166 of the rotor assembly 160 is configured with a computer 180 having user-interface software as would be adapted by those skilled in the art for 1) controlling and monitoring of the pulse sequencing aspects of the invention (e.g., RF, TTL, etc.), 2) controlling other operational aspects of the probe and equipment, 3) automating the collection of measurement data and/or measurement functions/capabilities, 4) conducting analyses, and 4) setting the accurate rotational frequency of the rotor assembly 160 up to a maximum of ~100 Hz. Depending on the size of the object under investigation, the rotation frequency is preferably selected to be in the range up to about 40 Hz, and more preferably at a frequency in the range from 0.01 Hz to 40 Hz.

The MAS probe 100 is also adapted for use, and may be equipped, with an optical detector system 190 for generating transistor-to-transistor logic (TTL) pulses. The TTL pulses serve to trigger corresponding RF pulse sequences coinciding with precision markings located on the rotor assembly 160. In one embodiment (FIG. 2A), the optical detector system 190 comprises a scintillation fiber for detecting motion of the rotor 160 in combination with precision markings located on the rotor assembly 160.

For applications involving fluid objects, preferred choices for RF pulse sequencing used in conjunction with the MAS probe 100 include phase-corrected magic angle turning (PHORMAT) or 2D-phase-adjusted spinning sidebands (PASS). The PHORMAT and PASS pulse sequencing are detailed in Hu et al., J. Magn. Reson. Med. 47, 829–836 (2002), hereby incorporated by reference.

It will be understood by those of ordinary skill in the art that due to the modular design of the present invention, minor modifications to the slow MAS probe 100, the rotor assembly 160, as well as other components (e.g., driving assembly 170) can be scaled dimensionally to accommodate a large variety of samples. For example, cells and cell clusters require very strong gradients and rotors with diameters of 1 mm or less. Analyses involving other cell systems, such as tissues, organs, and live animal specimens may require use of rotors 160 having diameters of 10 cm or greater. And, the largest of biological objects or specimens envisioned to be analyzed according to the probe and method of the present invention include the intact body of a human; rotor assemblies with diameters up to 60 cm or greater cm may be required for a proper analysis of the object of interest. Thus, a significant advantage of the MAS-gradient probe of the present invention is the modularity in size, dimensions, and bore.

In sum, the MAS-gradient probe of the present invention has direct application to analyses involving cells, cell systems, tissues, organs, and live specimens, including intact live animals. The probe is envisioned to be equally applicable to analyses involving the body of a human subject or patient. The following experimental examples illustrate the potential applications.

$^1$H NMR EXPERIMENTS

Example 1

$^1$H NMR experiments were performed using a horizontal wide-bore (30 cm) 2 Tesla Oxford magnet tuned to a proton Larmor frequency of 85 MHz, in combination with a Varian (Palo Alto, Calif.) Unity Plus console. In the present embodiment (FIG. 2A), the probe 100 had an O.D. of 120 mm, to fit in a standard gradient probe (not shown) inserted into the magnet. The rotor 160 comprised a custom-made (ARRK Product Development Group, Beaverton, Oreg.) epoxy photopolymer cylindrical mold 163 as described hereinabove and illustrated in FIG. 3. The mold 163 was cut into two halves to allow insertion of an animal specimen, in this case, a live, anesthetized female BALBc mouse. In the instant case, only the center part of the animal was probed and investigated. The outside diameter of the gradient probe was 220 mm and was shimmed using a shim probe (not shown) at room temperature. The rotor assembly 160 included a driving assembly 170 having a $\frac{1}{12}^{th}$ HP motor (Baldor Series 18H AC Flux Vector Controlled). The NMR coil 150 was of an Alderman-Grant coil design, hand-made of copper strips mounted on a first outside cylinder 161 of the rotor assembly 160 such that the RF field was perpendicular to both the rotor 160 axis and the external magnetic field $B_0$. The I.D. of the coil 150 was 3.4 cm and the overall length was 5.5 cm. The coil 150 was used for both transmitting and receiving, and was single-tuned to the proton Larmor frequency of 85 MHz. As shown in FIG. 2A, the NMR-sensitive area inside the coil 150 had a length of about 4 cm. The area between the dotted lines shown in FIG. 2B denotes the part of a mouse body that was probed, comprising the torso and the upper part of the belly of an anesthetized female BALBc mouse.

To adjust the magic angle, the rotor 160 and the optical detection (for synchronizing with the RF pulse sequence) system 190 (comprising a scintillating fiber) were mounted on a supporting member platform 159, which could be rotated around an axis perpendicular to the field direction. The magic angle was set by using a water sample inside a cylinder 162 with an O.D. of 5 mm and a length of 25 mm, placed in the center of the rotor 160. The static water line was broadened to about 180 Hz by susceptibility gradients induced by 230 micron glass beads submerged into the water. The magic angle was set by performing the PHORMAT experiments at a frequency of 2 Hz and minimizing the width of the isotropic line.

Prior to spinning, the BALBc mice were anesthetized with a mixture of 0.3 mL Xylazine [concentration of 20 mg/mL] and 1.0 ml of Ketamine [concentration of 100 mg/ml]. The cocktail mixture was administered via interperitoneal injection at 1.3 mL/kg mouse body weight. Anesthesia lasted for 1.0 to 1.5 hours. While anesthetized the animal's eyes were lubricated to prevent drying. Ample air was supplied to the animals via a tube inserted into the rotor 160 during spinning to prevent asphyxiation. In order to investigate the tolerance of mice for spinning, mice were spun at spin frequencies in the range from 1–8 Hz (magnet). Durations of up to 70 minutes were used while spinning at 1–2 Hz, and up to 40 minutes at higher speeds. No post-experimental morbidity or mortality occurred in any of the test animals; and, all animals continued to thrive and gain weight.

Example 2

FIG. 2B shows a picture of the probe 100 for a slow MAS experiment according to a second embodiment of the present invention. The probe 100 may be adapted and configured with incorporated gradient coils and with a longer rotor 160 to probe a whole body volume of a mouse positioned at the center of the magnet and the probe 100. For example, the outside diameter of the probe 100 without the gradients (FIG. 2A) is restricted to 120 mm, as it has to fit in a standard gradient probe with the same I.D. and an O.D. of 220 mm. By incorporating the gradients into the MAS probe, the standard gradient probe is no longer needed, which means that the diameter of the MAS-gradient probe can be increased to 220 mm. This is more than sufficient to perform research on all parts of a mouse, and probably a larger animal such as a rat as well. In fact, for a mouse MAS probe 100 the O.D. can be reduced to 150 mm, which makes it possible to mount this probe 100 in many high-field magnets (up to 12 Tesla) with a (horizontal) bore diameter of this size. Further, the need for a room temperature shim probe may be optional if the magnet can be shimmed adequately by the various gradient coil(s) combined with optimized MAS sample spinning.

The probe 100 may be configured for use and/or fit into magnets with any strength available to date and may be so configured and/or adapted for use in the bore of the magnet, with sizes varying from a few cm (e.g., 4 cm) (for research on small fluid samples), up to tens of cm (e.g., 60 cm) (for specimens of the size of a human or greater). Thus, the magnet is operable on specimens and animals of increasingly and significantly larger size and volume (e.g., rats, rabbits, human, etc.), making the probe 100 widely applicable for in vitro and in vivo applications. And, as noted hereinabove, the probe 100 is adaptable and operable for conducting in vivo measurements of a whole animal, not just sections (e.g., center, middle, or end sections) of the animal given that in the present embodiment of the MAS probe 100, the gradient coil assembly 120 (housing the gradient coils) is incorporated. Also, the gradient coils of the assembly 120 are smaller in volume than are used in standard gradient probes. Thus, larger gradients are possible than envisioned by the probe in Example 1, or other state-of-the-art probes.

PHORMAT Experiments

The PHORMAT technique is based on a Magic Angle Hopping (MAH) approach detailed in Bax et al., J. Magn. Reson. 1983; 52: 147, whereby a sample is hopped over angles of 120° about an axis at the magic angle. Prior to each hop, RF storage pulses are applied to orient the magnetization parallel to the external magnetic field $B_0$ during consecutive hopping periods. Before, in-between, and after two hops, the magnetization is allowed to de-phase in the transverse plane for a variable evolution time. With a proper phase cycling of the RF pulses and the receiver phases, the MAH experiment produces a conventional 2-dimensional (2D) isotropic-anisotropic correlation spectrum, wherein the isotropic line widths are free from the anisotropy broadening.

Figure 6:
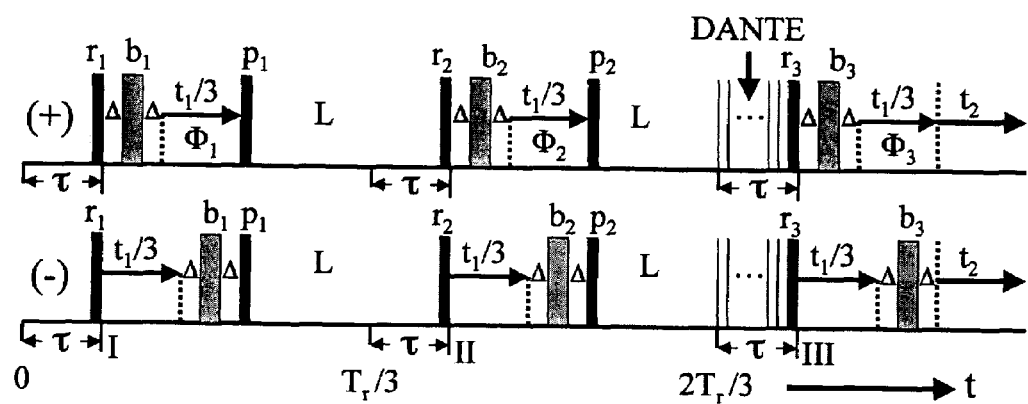
FIG. 6 shows a preferred PHORMAT RF Pulse sequence employing a DANTE water suppression technique according to a method of the present invention. The parameter $T_r$ denotes the rotation period of the sample, $t_1$ is the variable evolution time, $t_2$ is the acquisition time, $r_1$, $r_2$, and $r_3$ refer to the 90° pulses synchronized to a value of ⅓ of the rotor period, respectively.

A preferred PHORMAT experiment is a variant of the original MAT experiment (as described in Gan Z, "High-resolution Chemical Shift and Chemical Shift Anisotropy Correlation in Solids Using Slow Magic Angle Spinning": J. Am. Chem. Soc. 1992; 114: 8307–8309), incorporated herein by reference, which is further considered a variant of MAH, whereby the sample is rotated slowly and continuously instead of hopped, and the effect of 120° hopping is achieved by synchronizing the pulses in a preferred mode at about ⅓ of the rotor period. The continuous rotation makes the PHORMAT methodology simpler and easier to implement than MAH. FIG. 6 shows a preferred PHORMAT RF pulse sequence selection mode for the experiments according to an embodiment of the present invention. The parameter $T_r$ denotes the rotation period of the sample, $t_1$ is the variable evolution time, and $t_2$ is the acquisition time. The 90° pulses labeled $r_1$, $r_2$, and $r_3$ are synchronized to the preferred value of about ⅓ of the rotor period, whereby the magnetization is rotated into the transverse plane. During the evolution periods $t_1/3$, the magnetization precesses through angles $\Phi_1$, $\Phi_2$, and $\Phi_3$, respectively. The 90° pulses ($p_1$ and $p_2$) represent storage pulses which project either the $\cos(\Phi_i)$ or the $\sin(\Phi_i)$ (i=1,2,3) component of the precessing magnetization (after the corresponding $t_1/3$ period) to the z-axis, where it remains during the storage periods (labeled L). A free induction decay (FID) is acquired following the last 90° pulse ($r_3$). For fields (local) arising from any second-rank interactions (such as the magnetic susceptibility fields), summation of the precession angles ($\Phi_1$, $\Phi_2$, and $\Phi_3$) averages to the isotropic values of the interactions (i.e. $\Phi_1+\Phi_2+\Phi_3=\omega_{iso}t_1$). With a proper phase cycling of the first 90° pulse $r_1$, the projection pulses $p_1$ and $p_2$, and the receiver (see Hu J Z, Wang W, Liu F, Solum M S, Alderman D W, Pugmire R J, Grant D M. Magic-angle-turning experiments for measuring chemical-shift-tensor principal values in powdered solids. J Magn Reson 1995; A 113: 210–222), the FID can be expressed as follows:

$$FID(t_2,t_1)=\exp(-i\omega_{iso}t_1)FID(t_2)$$

Fourier transformation as a function of $t_2$ (and then as a function of $t_1$) yields a pure absorption-mode 2D spectrum.

Other features of the PHORMAT sequencing are the 180° pulses ($b_1$, $b_2$, and $b_3$) placed before (+) or after (−) the three phase-accumulation periods, which prevents distortions in the FID due to the receiver dead-time, thus improving the base plane of the 2D spectra, and the application of a DANTE water-suppression sequence. The start of the PHORMAT sequence is triggered by a transistor-to-transistor logic (TTL) signal generated from an optical detection system 190 which serves as a trigger pulse for the RF pulse sequences that are synchronized to precision markers located on the rotor assembly 160. Position of the mouse is synchronized with the start of the DANTE water-suppression sequence, which improves the water-suppression efficiency as it prevents the shifting in the resonance frequency of the water line (from increment to increment) arising from position-dependent magnetic susceptibility fields in the animal.

In order to obtain adequate water suppression, the duration τ of the DANTE sequence is preferably selected to be at least 200 msec. This reduces the maximum spinning speed that can be used. As is shown in FIG. 2, $T_r \approx 3\tau + t_1$, if the time Δ and the pulse durations can be neglected. As the maximum evolution time is 60 msec, the spinning speed used is restricted to 1.5 Hz or less. This experiment may be regarded as a worst-case scenario for studying the viability of the in vivo PHORMAT approach because of the increased $B_o$ inhomogeneity over the relatively large volume and because of the presence of the lung cavity in the volume of interest, where the susceptibility broadening in the surrounding tissues are increased. Other alternative water suppression techniques such as CHESS that employ a short duration pulse sequence may also be applicable (see Moonen et al., *Water Suppression in Proton MRS of Humans and Animals*; In: Young IR, editor. Methods in Biomedical Magnetic Resonance Imaging and Spectroscopy. New York: John Wiley & Sons; 2000. p.791–810).

Figure 7:
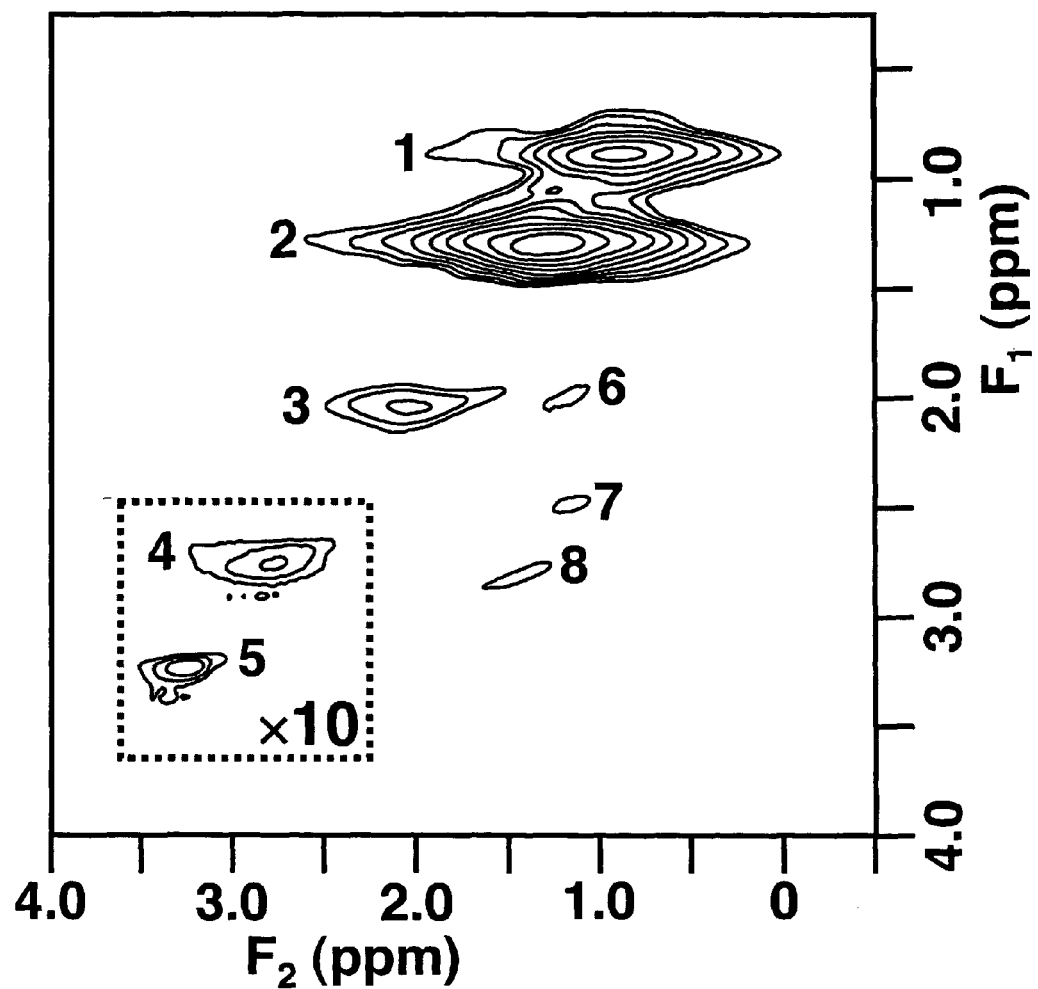
FIG. 7 shows a typical two-dimensional PHORMAT metabolite spectrum obtained while spinning a live mouse at a frequency of 1.5 Hz about the magic axis. $F_1$ and $F_2$ denote the isotropic (evolution) and anisotropic (acquisition) dimension, respectively.

FIG. 7 shows a resulting 2D PHORMAT spectrum obtained while spinning a live mouse at a frequency of 1.5 Hz about the magic axis. $F_1$ and $F_2$ represent the isotropic (e.g., evolution) and anisotropic (e.g., acquisition) dimensions, respectively. Signal information is contained near the diagonal axis. The spectrum is dominated by the signals arising from the triacylglycerols and other lipids present in the adipose tissue, muscles, and other areas of and in the body. In the figure, five main resonances are identified (labeled as 1, 2, 3, 4, and 5). The intensities of the 2D area around the relatively weak signals (e.g., 4 and 5) were enhanced by a factor 10 in order to view the signals. Other small intensity peaks (labeled 6, 7, and 8), arising at about 1.3–1.5 ppm in the $F_2$ direction were also observed. These lines appear to be associated with the relatively strong signal 2, and have an intensity of about 5% of that of the main 1.3 ppm peak. These signals may be due to imperfections in the PHORMAT experiment or an incomplete dephasing of the magnetization after the storage times. However, they do not pose any analysis problem as they arise outside the area of interest (e.g., area containing the actual signal information in the 2D spectrum).

Figure 8:
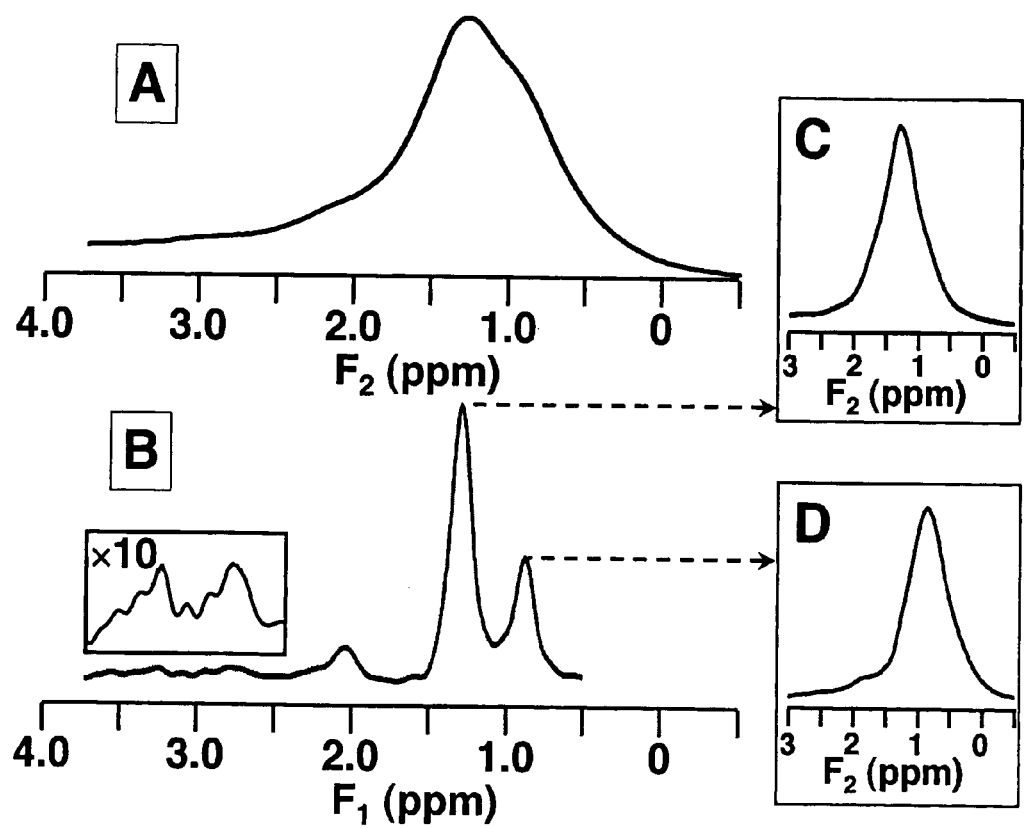
FIG. 8A shows a PHORMAT metabolite spectrum using a slow MAS probe according to an embodiment of the present invention. The spectrum was obtained by projecting the 2D spectrum along the anisotropic ($F_2$) axis, while spinning a live mouse at a frequency of 1.5 Hz about the magic axis, where the anisotropic projection is the same as the spectrum obtained in a stationary mouse.
FIG. 8B shows a PHORMAT metabolite spectrum using a slow MAS probe according to an embodiment of the present invention. The high-resolution spectrum was obtained by projecting the 2D spectrum along the isotropic ($F_1$) axis.
FIG. 8C shows a PHORMAT metabolite spectrum using a slow MAS probe according to an embodiment of the present invention. The high-resolution spectrum shows the individual anisotropic spectra of the peaks at 1.3 ppm.
FIG. 8D shows a PHORMAT metabolite spectrum using a slow MAS probe according to an embodiment of the present invention. The high-resolution spectrum shows the individual anisotropic spectrum of the peaks at 0.9 ppm.

In FIG. 7, the widths of the resonance lines in the $F_2$ direction are considerably larger than those in the $F_1$ direction. This is also shown in FIG. 8, where the anisotropic projections (FIG. 8A), which are the same as the spectrum obtained in a stationary mouse, the isotropic projection (FIG. 8B), and the individual anisotropic lines of the 1.3 ppm line (FIG. 8C) and 0.9 ppm line (FIG. 8D) are given. The widths of the anisotropic lines in FIG. 8C and FIG. 8D are about 60 Hz, while the corresponding isotropic line widths are about 13 Hz. Hence in the 2 T field, the PHORMAT experiment reduces the apparent line widths by a factor 4.6. Similar results were obtained for the other peaks.

It is important to note that in any experiment involving ultra-slow magic angle spinning, the shimming of the external magnetic field should not be carried out on a stationary sample when the static line width is dominated by quantities such as the magnetic susceptibility gradients, since the external shim coils then produce macroscopic gradients to minimize the susceptibility broadening, which are not averaged out by the spinning. An increased isotropic line width may thus be observed in an ultra-slow spinning experiment such as PHORMAT. To minimize the anisotropy, the magnet should be shimmed using a rotor 160 entirely filled with water or another liquid so as to minimize the potential susceptibility broadening. Then the observed line width will be largely determined by the external field inhomogeneity, which may be minimized with shimming. For in vivo PHORMAT, this procedure has the additional significant advantage that no time has to be spent on shimming while the object of interest is positioned in the magnet, and all the available measuring time can be used for MR spectroscopy. In the preferred embodiment, the magnet was shimmed by replacing the mouse mold with an 81 mm long cylinder with an I.D. of 20 mm, entirely filled with water. In stationary samples, a line width of 8 Hz was obtained, which is in part caused by a residual field inhomogeneity. It is likely PHORMAT reduces this isotropic line width further, as the experiment also eliminates part of this inhomogeneity. For example, results showed that after shimming, the static line width was 3.9 Hz, and that the isotropic line width obtained in a 1.5 Hz PHORMAT experiment was reduced to 0.6 Hz. If the same line width reduction were to be obtained in the large sample volume, the static line width of 8 Hz would be reduced to 1.2 Hz in the isotropic PHORMAT spectrum, which is considerably less than the intrinsic line widths usually observed in intact biological samples. Hence, another important advantage of the PHORMAT approach is that larger voxel sizes can be selected in a "volume-selective" PHORMAT experiment without compromising the line widths by the increased field inhomogeneity, presuming that the larger voxel size does not induce increased tissue heterogeneity.

Example 3

A freshly excised rat liver was analyzed using a 1 Hz PHORMAT experiment with a 7 T magnetic field. Results were compared with those previously obtained. In the present case (liver), the anisotropic line width of the 0.9 ppm peak was found to be 150 Hz, whereas in the mouse, a value of 60 Hz was observed in the 2 T field. As noted previously, the line broadening in biological objects is dominated by magnetic susceptibility and the anisotropic line width is approximately proportional to the external field. As a result, at 7 T, a line width of 210 Hz is predicted, which is larger than that found in the liver. The increased broadening in the mouse may be due to signals arising from tissues close to cavities like the lungs, where the susceptibility gradients are presumably larger than in the more homogeneous liver sample. The isotropic line width in the excised liver is 15 Hz, close to the 13 Hz width measured in the live mouse at 2 T. This is in agreement with the fact that the isotropic line width is more or less field independent. In fact, the main field dependence in this line width arises from the diffusion-induced line broadening. In a theoretical evaluation that will be published elsewhere it will be shown that this broadening is proportional to $GD^{1/2}$, where G is the susceptibility gradient and D is the diffusion coefficient. As G increases linearly with the external field, the broadening is proportional to the external field as well. The diffusion-induced broadening was estimated to be about 5 Hz for the liver in 7 T field and room temperature, which means that in the 2 T field at 37° C., this broadening is reduced to 1.5 Hz. Hence this broadening contributes only 12% to the observed line width.

Example 4

In order to evaluate the possible impact of respiratory, cardiac, and blood flow motions in the mouse body, a PHORMAT spectrum was obtained on the anesthetized mouse. Subsequently, the host mouse was euthanized with $CO_2$. A second PHORMAT experiment was then performed as in the PHORMAT experiment of Example 2 above. The spectrum (not shown) was virtually identical to the one obtained on the live animal (FIG. 7), indicating that at least for this experiment, where a large part of the body was used for spectroscopy, the impact of internal motions in the animal were negligible and may be neglected from an analysis standpoint.

In sum, it has been shown that even in a relatively low 2 T field in vivo PHORMAT using ultra-slow spinning frequencies results in a substantial increase in the resolution of the $^1H$ MR metabolite spectra. This technique thus has the potential to significantly enhance the utility of proton MR spectroscopy for biochemical and biomedical research in live animals. It also enhances the utility of high-field small animal imaging instruments (at present field strengths up to 11.7 T are commercially available), as the anisotropic line width, which increases linearly with the field, is eliminated in the isotropic dimension. As a result the resolution of the spectrum in the isotropic dimension increases more or less proportional with the field, provided that the spinning speed has been chosen sufficiently large so that diffusion-induced broadening, which is also proportional to the field, is small compared with the intrinsic, field-independent, line width. Moreover, PHORMAT makes it possible to determine separately the anisotropic line shapes of the individual metabolites that are often overlapping in a standard MR spectrum. This should increase the biomedical utility of this information. The question arises whether the PHORMAT approach can be used in the hospital to investigate patients as well. In principle, the rotation of a patient at ultra-low frequencies should cause no harm. For instance, if a patient were to be placed in a cylinder with a radius of 30 cm, a spinning frequency of 1 Hz would induce a centrifugal force of only 1.2 G at the perimeter of the patient (usually the shoulders). If the head of the patient were stabilized near the middle of the cylinder, the centrifugal forces in the head would be considerably less, on the order of 0.4 G. Also, as explained above, the time-dependence in the external field experienced by a patient would be relatively small, 15 T/sec when spinning at 1 Hz in a 3 T field. The main problem in this case is the design of a magnet with its bore along the magic axis. As an alternative to rotation of the patient, the external magnetic field could be rotated either mechanically or electronically by generating both a static and a rotating field component. Also, if a very slow spinning of the patient were acceptable, both the patient and the magnetic field could be rotated in opposite directions. In the latter configuration, it would be conceivable to realize even rotation speeds greater than 1 Hz.

2-D PASS Experiments

Figure 9:
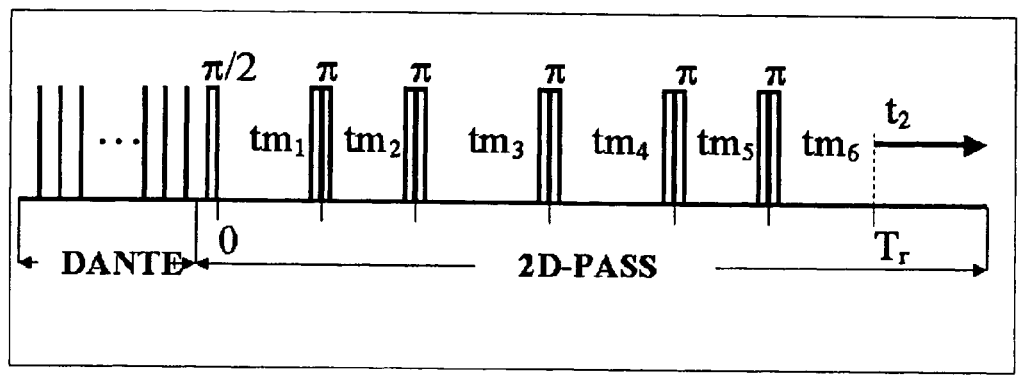
FIG. 9. illustrates a 2-D PASS metabolite spectrum used in combination with a DANTE water suppression sequence. The timings are counted from the middle of the $\pi$ pulses.

PASS is a one-rotor-period constant evolution time 2D experiment, during which five $\pi$ pulses are applied, with time intervals $tm_1$ to $tm_6$. FIG. 9 shows the PASS R.F. pulse sequence used for the studies of biological samples. In PASS, the center band spectrum and the SSB spectra are separated by order. This is achieved by acquiring the signal after a series of PASS experiments with different values of the time intervals $tm_1$ to $tm_6$. Each combination of time intervals has been chosen in such a way that the contribution of the signal in the observed free induction decay (FID) in the acquisition dimension ($t_2$), arising from the center band and SSBs, is proportional to a phase factor given by exp $(-ik\Theta)$, where k denotes the sideband order and $\Theta$ is a variable called "pitch". Then the FID, acquired on an isotropic sample (e.g., a powder sample) can be written as $$FID(\Theta, t_2) = \sum_{k=-\infty}^{k=\infty} a^{(k)} \exp(-ik\Theta) \exp(i(\omega_{iso} + k\omega_r)t_2) \quad [1]$$

$$\exp\left(-\frac{T_r + t_2}{T_2}\right),$$

where $a^{(k)}$ is the powder-averaged amplitude of the center band (k=0) or the k-th side band, observed in a traditional MAS experiment, $\omega_{iso}$ is the isotropic frequency, $\omega_r$ is the angular spinning frequency of the sample, $T_r$ is the rotor period, and $T_2$ is the spin-spin relaxation time. If $\theta/2\pi$ is continuously varied between 0 and $\infty$, the 2D Fourier transform (FT) of Eq.[1] becomes $$f(\omega_1, \omega_2) = \sum_{k=-\infty}^{k=\infty} a^{(k)} \exp\left(-\frac{T_r}{T_2}\right) \quad [2]$$

$$\int_0^\infty \exp(i\omega_1 \Theta) \exp\left(-i2\pi k \frac{\Theta}{2\pi}\right) d\frac{\Theta}{2\pi} \times$$

$$\int_0^\infty \exp(i\omega_2 t_2) \exp(i(\omega_{iso} + k\omega_r)t_2) \exp\left(-\frac{t_2}{T_2}\right) dt_2$$

$$= \sum_{k=-\infty}^{k=\infty} a^{(k)} \exp\left(-\frac{T_r}{T_2}\right) \delta(\omega_1 - 2\pi k)$$

$$\frac{\frac{1}{T_2} + i(\omega_2 + \omega_{iso} + k\omega_r)}{\left(\frac{1}{T_2}\right)^2 + (\omega_2 + \omega_{iso} + k\omega_r)^2}$$

The absorption component of Eq.[2] is given by Eq. [3] below:

$$f(\omega_1, \omega_2) = \sum_{k=-\infty}^{k=\infty} a^{(k)} \exp\left(-\frac{T_r}{T_2}\right) \delta(\omega_1 - 2\pi k) \quad [3]$$

$$\frac{\frac{1}{T_2}}{\left(\frac{1}{T_2}\right)^2 + (\omega_2 + \omega_{iso} + k\omega_r)^2},$$

where $\delta(\omega_1 - 2\pi k)$ is a delta function, producing a non-zero signal intensity at $\omega_1 = 2\pi k$, or $f_1 = k$. It follows that a series of spectra is obtained that separates the contributions for each k value, i.e. it separates the center band and side band spectra. In practice (as described by Antzutkin et al. in "Two-dimensional Sideband Separation in Magic-angle-Spinning NMR in J. Magn. Reson. 1995, A115: 7–19), it suffices to use "n" discrete values of $\theta$, varying from 0 and $2\pi$ (in steps of $2\pi/n$), where n denotes the total number of center-band and side-band spectra to be resolved. Hence, "n" PASS sequences must be performed with a set of n different values of $tm_1$-$tm_6$, which can be calculated by solving the so-called PASS equation. Then discrete 2D FT of Eq. [1] with exactly n points along the $\theta/2\pi$ dimension correctly samples the traces at the order of the sideband frequency, and the resulting set of spectra, given by Eq. [3], is obtained again. If n is chosen smaller than the total number of SSBs that have to be separated, folding effects occur, i.e., spectra arising from SSBs of orders larger than (n/2)-1 are folded into the SSB spectra with orders equal to or larger than -n/2, while spectra arising from SSBs of orders less than -n/2 are folded into the SSB spectra with orders equal to or less than n/2-1. In short, in order to produce a clean separation of the SSB spectra, the first point of FID along the $\theta/2\pi$ dimension needs to be multiplied by 1 instead of 0.5 as would be used in some commercial spectrometers. Hence in some cases a modification in the FT software is required to obtain distortion-free PASS spectra.

Compared with Single Pulse MAS (SP-MAS) and PHOR-MAT, PASS has some advantages and disadvantages. The main advantages are: (I) PASS is a sensitive method, providing nearly the same signal-to-noise ratio (SNR) per unit measuring time as that of a SP-MAS experiment. (II) PASS requires relatively short measuring times. In order to compensate for pulse imperfections or a R.F. field inhomogeneity, a phase cycling sequence has to be applied. In principle each evolution step in the PASS experiment requires 96 phase-cycling steps, which can result in relatively long measuring times. For instance, if 16 evolution steps and a recycle delay of 1 sec are used, the measuring time becomes about 26 minutes. However, in practice the amount of phase cycling steps can be reduced to 16 or even less without causing major spectral degradations, reducing the measuring to 4 minutes or less. This makes it possible to extend PASS with other R.F. pulse sequences and pulsed field gradients to determine the $T_1$, $T_2$, $T_{1\rho}$ (the rotating-frame relaxation time), and diffusion coefficients of the individual metabolite peaks. All these experiments make it possible to improve the quantitative analysis of the observed spectra. Moreover, the amount of different $\theta/2\pi$ steps, and, henceforth, the measuring time, can be reduced if less sidebands are observed. Hence it is advisable to spin the sample at the maximum allowable spinning speed without compromising the structural and compositional integrity of the sample. This is especially important in large external field strengths, as the susceptibility broadening, and therefore the amount of SSBs at a given spinning speed, increases proportional to $B_0$.

The main disadvantages of PASS are: (I) The spinning speed cannot arbitrarily be reduced. In PASS the magnetization is constantly present in the transverse plane, and the first signal is observed after one rotor period. This means that the amplitude of the signal is reduced as a result of the decay of the magnetization during this period, which is governed by the spin-spin relaxation time $T_2$ associated with the isotropic line width. Therefore serious signal attenuation occurs when the spinning rate is comparable to or less than $(1/T_2)$. Moreover, spectral distortions occur if the $T_2$ values of the different spectral lines are not the same. For instance, in the liver sample we found $T_2$ values of the various metabolite peaks in the range 30–70 msec, which means that for this tissue spinning speeds of 30 Hz or larger should be used. Similar results were found in tissues excised from other organs. (II) At spinning rates below 30 Hz phase distortions in the spectra, resulting from prolonged time-evolutions due to homonuclear J-coupling that are not refocused by the $\pi$ pulses, are observed. This is another reason to use larger speeds. (III) As mentioned above, Eq.[1] is derived for an isotropic sample such as a powder. For an anisotropic sample this equation no longer applies, and the sideband and centerband spectra are longer separated by order and contain contributions from the other spectra. However, it was observed that such 'leakages' for liver and other tissues are very minor. Apparently these samples are sufficiently homogeneous to avoid these problems. Moreover, this problem can be solved by synchronizing the pulse sequence with the rotor position and by moving the start of the pulse sequence forward in time in exact synchrony with the increasing pitch θ/2π of the pulse sequence.

Figure 10:
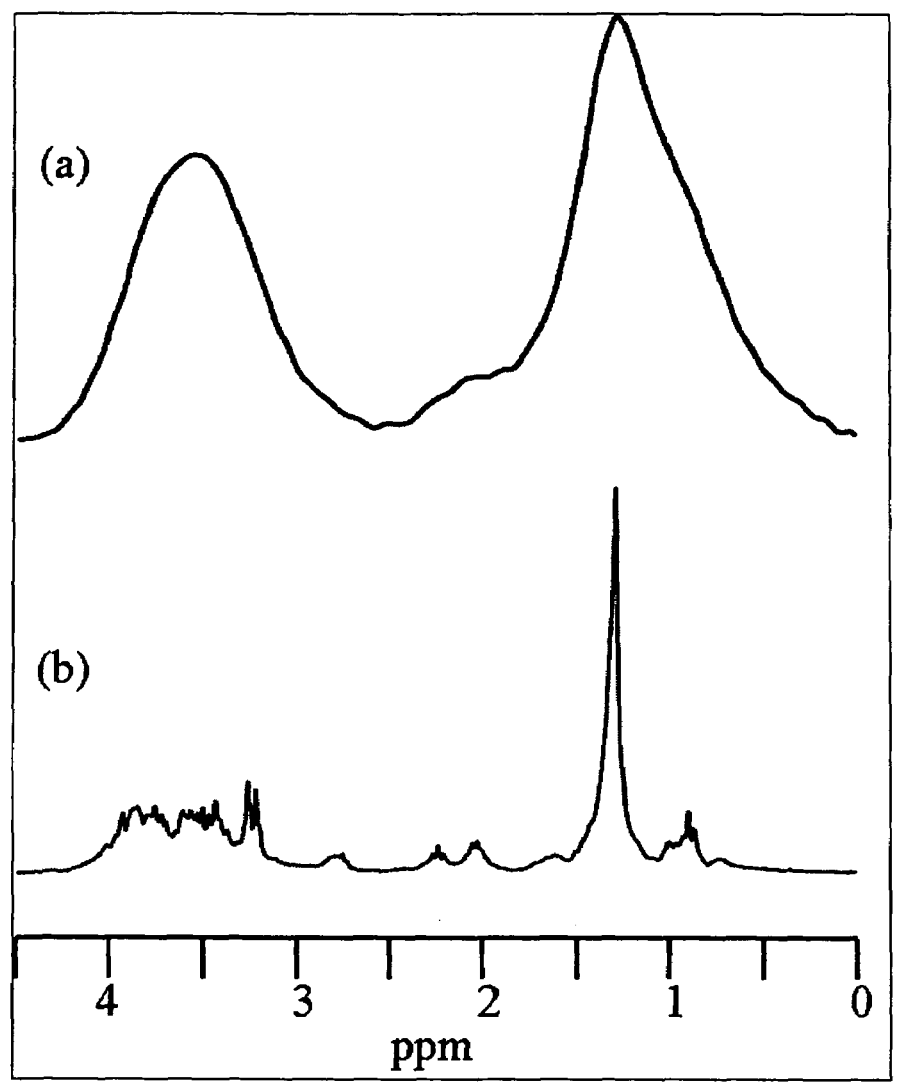
FIG. 10A illustrates a typical water-suppressed $^1$H spectrum obtained on a static sample of freshly excised rat liver (~200 mg) at a magnetic field of 7 T.
FIG. 10B. illustrates a typical $^1$H 2-D PASS spectrum obtained on a sample of freshly excised rat liver (~200 mg) at a magnetic field of 7 T. The spectrum was taken at a spinning rate of 40 Hz.

FIG. 10A shows an example of a $^1$H spectrum obtained from a freshly excised rat liver at a 7 T magnetic field. FIG. 10B gives the corresponding $^1$H PASS spectrum obtained using a spinning speed of 40 Hz. It follows that the spectral resolution in the PASS spectrum (FIG. 10B) is significantly enhanced compared with the static spectrum (FIG. 10A). Actually the resolution in the PASS spectrum is somewhat better than that obtained in a standard fast SP-MAS experiment, which may be caused by the intrinsic $T_2$ weighting in the PASS experiment resulting in an apparent line narrowing if the FID contains a fast-decaying component, or by sample distortions arising during fast spinning, where the centrifugal forces can drive part of the sample to the rotor edges and where the $B_0$ homogeneity is reduced. However, more research is needed to fully resolve this issue.

In summary, for small size biological objects such as excised tissues, organs, live bacterial cells and biofilms, PASS at a spinning rate of about 30 Hz and above is preferred. For in vivo studies of large size biological objects such as live mice, rats, etc., PHORMAT applied at a spinning rate of 1–3 Hz is a preferred.

Closure

While the preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

We claim:

1. A probe useful for slow Magic Angle Spinning Magnetic Resonance Imaging and Spectroscopy, the probe comprising:
   (a) at least one base member for supporting said probe;
   (b) a shielding member mounted to said base member;
   (c) at least one gradient assembly comprising a plurality of gradient coil(s) housed within said shielding member mounted to said base member;
   (d) an RF circuit assembly comprising at least one R.F. NMR coil(s) mounted to said member;
   (e) a rotor assembly for spinning a specimen, said assembly disposed so as to be in optimum alignment with said gradient coil(s) and said NMR coil(s);
   (f) a driving assembly operably connected with said rotor assembly for driving said rotor assembly;
   (g) a monitoring system comprising a respiratory plethysmograph operably disposed for monitoring respiration and/or respiratory motions of an animal or other living specimen being rotated or subjected to a rotating magnetic field; and
   (h) wherein said rotor assembly is rotatable about an axis positioned at a magic angle of 54.44° relative to an applied magnetic field Bo, at spin speeds of less than 100 Hz.

2. A probe useful for slow Magic Angle Spinning Magnetic Resonance Imaging and Spectroscopy, the probe comprising:
   (a) at least one base member;
   (b) a shielding member mounted to said base member;
   (c) at least one gradient assembly comprising a plurality of gradient coil(s) housed within said shielding member mounted to said base member;
   (d) an RF circuit assembly comprising at least one R.F. NMR coil(s) mounted to said base member;
   (e) a rotor assembly for spinning a specimen, said assembly disposed so as to be in optimum alignment with said gradient coil(s) and said NMR coil(s);
   (f) a driving assembly operably connected with said rotor assembly for driving said rotor assembly;
   (g) an optical detector system having transistor-to-transistor logic pulse sequencing whereby said sequencing is adapted to tagger corresponding RF pulse sequencing in synchronization with precision markers mounted on said rotor assembly; and
   (h) wherein said rotor assembly is rotatable about an axis positioned at a magic angle of 54.44° relative to an applied magnetic field Bo, at spin speeds of less than 100 Hz.

3. A probe useful for Magnetic Resonance Imaging and Spectroscopy, the probe comprising:
   (a) at least one base member for supporting said probe;
   (b) a shielding member mounted to said base member;
   (c) at least one gradient assembly comprising a plurality of gradient coil(s) housed within said shielding member mounted to said base member;
   (d) an RF circuit assembly comprising at least one R.F. NMR coil(s) mounted to said base member;
   (e) a rotor assembly for spinning a specimen, said rotor assembly comprising a first and second cylinder, said second cylinder being adapted for insertion of a cylindrical mold for mounting an animal or other living specimen snugly within said rotor, said assembly disposed so as to be in optimum alignment with said gradient coil(s) and said NMR coil(s);
   (f) a driving assembly operably connected with said rotor assembly for driving said rotor assembly; and
   (g) wherein said rotor assembly is rotatable about an axis positioned at a magic angle of 54.44° relative to an applied magnetic field Bo, at spin speeds of less than 100 Hz.

4. A probe useful for slow Magic Angle Spinning Magnetic Resonance Imaging and Spectroscopy, the probe comprising:
   (a) at least one base member for supporting said probe;
   (b) a shielding member mounted to said base member;
   (c) at least one gradient assembly comprising a plurality of gradient coil(s) housed within said shielding member mounted to said base member;
   (d) an RF circuit assembly comprising at least one R.F. NMR coil(s) mounted to said base member;
   (e) a rotor assembly for spinning a specimen, said rotor assembly comprising a first and second cylinder, said second cylinder being adapted for insertion of an epoxy photopolymer cylindrical mold for mounting an animal or other living specimen snugly within said rotor, said assembly disposed so as to be in optimum alignment with said gradient coil(s) and said NMR coil(s);
   (f) a driving assembly operably connected with said rotor assembly, said driving assembly comprising three sets of pulleys for rotating said rotor assembly, a $1^{st}$ set comprising a single pulley, a $2^{nd}$ set comprising two pulleys, and a $3^{rd}$ set comprising a single pulley, wherein said pulley in said $1^{st}$ set is attached to said rotor, said $2^{nd}$ set has a single rotational axis whereby said pulleys rotate in opposite directions whereby the axis of said $2^{nd}$ set of pulleys is perpendicular to the rotational axis of said $1^{st}$ set, and whereby said $3^{rd}$ set is operably connected to said driving motor to spin said rotor in an optimal driving arrangement; and (g) wherein said rotor assembly is rotatable about an axis positioned at a magic angle of 54.44° relative to an applied magnetic field Bo, at spin speeds of less than 100 Hz.

5. A probe useful for slow Magic Angle Spinning Magnetic Resonance Imaging and Spectroscopy, the probe comprising:

(a) at least one base member for supporting said probe;

(b) at least one gradient assembly comprising a plurality of gradient coil(s) mounted to said base member;

(c) an RF circuit assembly comprising at least one R.F. NMR coil(s) mounted to said base member;

(d) a rotor assembly for spinning a specimen, said assembly disposed so as to be in optimum alignment with said gradient coil(s) and said NMR coil(s);

(e) a driving assembly operably connected with said rotor assembly for driving said rotor assembly, said driving assembly comprising a driving belt and at least one rotor pulley configured to spin said rotor in an optimal driving arrangement;

(f) an optical detector system having transistor-to-transistor logic pulse sequencing operably disposed for triggering corresponding RF pulse sequencing in synchronization with precision markers mounted on said rotor assembly;

(g) a computer-controlled monitoring system operably disposed for collecting sample measurement data, said monitoring system comprising a respiratory plethysmograph operably disposed for monitoring respiration and/or respiratory motions of an animal or other living specimen; and (h) wherein said rotor assembly is rotatable about an axis positioned at a magic angle of 54.44° relative to an applied magnetic field Bo at spin speeds of less than 100 Hz and wherein said rotor assembly comprises a first and second cylinder, said second cylinder comprising a specimen holder moveable within said second cylinder for centering a volume of interest of said specimen within a homogeneous region of: i) a magnet providing said magnetic field Bo ii) said NMR coils iii) and/or said gradient coils within said rotor.

\* \* \* \* \*